United States Patent
Kiichiro

(10) Patent No.: US 8,569,357 B2
(45) Date of Patent: Oct. 29, 2013

(54) TAXANE PRO-EMULSION FORMULATIONS AND METHODS MAKING AND USING THE SAME

(75) Inventor: Nabeta Kiichiro, Setagaya-ku (JP)

(73) Assignee: Teikoku Pharma USA, Inc., San Jose, CA (US)

( * ) Notice: Subject to any disclaimer, the term of this patent is extended or adjusted under 35 U.S.C. 154(b) by 215 days.

(21) Appl. No.: 13/030,495

(22) Filed: Feb. 18, 2011

(65) Prior Publication Data

US 2011/0207803 A1 Aug. 25, 2011

Related U.S. Application Data

(60) Provisional application No. 61/306,315, filed on Feb. 19, 2010.

(51) Int. Cl.
| | |
|---|---|
| A61K 31/337 | (2006.01) |
| A61K 9/107 | (2006.01) |
| A61K 31/385 | (2006.01) |
| A61K 9/66 | (2006.01) |
| A01N 43/02 | (2006.01) |

(52) U.S. Cl.
USPC .......................... 514/449; 424/455

(58) Field of Classification Search
USPC .......................... 514/449; 424/455
See application file for complete search history.

(56) References Cited

U.S. PATENT DOCUMENTS

| | | |
|---|---|---|
| 5,399,363 A | 3/1995 | Liversidge et al. |
| 5,403,858 A | 4/1995 | Bastard et al. |
| 5,407,683 A | 4/1995 | Shively |
| 5,415,869 A | 5/1995 | Straubinger et al. |
| 5,438,072 A | 8/1995 | Bobee et al. |
| 5,439,686 A | 8/1995 | Desai et al. |
| 5,498,421 A | 3/1996 | Grinstaff et al. |
| 5,560,933 A | 10/1996 | Soon-Shiong et al. |
| 5,616,330 A | 4/1997 | Kaufman et al. |
| 5,626,867 A | 5/1997 | Eibl et al. |
| 5,698,582 A | 12/1997 | Bastart et al. |
| 5,733,888 A | 3/1998 | Carver et al. |
| 5,750,561 A | 5/1998 | Bastart et al. |
| 5,770,222 A | 6/1998 | Unger et al. |
| 5,785,976 A | 7/1998 | Westesen et al. |
| 5,858,410 A | 1/1999 | Muller et al. |
| 5,877,205 A | 3/1999 | Andersson |
| 5,902,610 A | 5/1999 | Hausheer et al. |
| 5,925,669 A | 7/1999 | Katz et al. |
| 5,929,030 A | 7/1999 | Hamied et al. |
| 5,972,992 A | 10/1999 | Carver et al. |
| 5,977,164 A | 11/1999 | Carver et al. |
| 6,071,952 A | 6/2000 | Owens et al. |
| 6,090,844 A | 7/2000 | Han et al. |
| 6,090,955 A | 7/2000 | Reszka et al. |
| 6,096,331 A | 8/2000 | Desai et al. |
| 6,107,333 A | 8/2000 | Andersson |
| 6,118,011 A | 9/2000 | Mayhew et al. |
| 6,121,234 A | 9/2000 | Benet et al. |
| 6,121,245 A | 9/2000 | Firshein |
| 6,207,178 B1 | 3/2001 | Westesen et al. |
| 6,218,374 B1 | 4/2001 | Rubinfeld |
| 6,346,233 B1 | 2/2002 | Knight et al. |
| 6,348,215 B1 | 2/2002 | Straubinger et al. |
| 6,348,491 B1 | 2/2002 | Chu et al. |
| 6,391,832 B2 | 5/2002 | Lyons et al. |
| 6,458,373 B1 | 10/2002 | Lambert et al. |
| 6,500,461 B2 | 12/2002 | Perkins et al. |
| 6,506,405 B1 | 1/2003 | Desai et al. |
| 6,531,139 B1 | 3/2003 | Gao et al. |
| 6,537,579 B1 | 3/2003 | Desai et al. |
| 6,538,019 B1 | 3/2003 | Nakajima et al. |
| 6,605,298 B1 | 8/2003 | Leigh et al. |
| 6,610,317 B2 | 8/2003 | Straub et al. |
| 6,638,973 B2 | 10/2003 | Holton |
| 6,660,286 B1 | 12/2003 | Lambert et al. |
| 6,667,048 B1 | 12/2003 | Lambert et al. |
| 6,720,001 B2 | 4/2004 | Chen et al. |
| 6,727,280 B2 | 4/2004 | Palepu et al. |
| 6,749,868 B1 | 6/2004 | Desai et al. |
| 6,753,006 B1 | 6/2004 | Desai et al. |
| 6,761,901 B1 | 7/2004 | Betageri et al. |
| 6,761,903 B2 | 7/2004 | Chen et al. |
| 6,932,983 B1 | 8/2005 | Straub et al. |
| 6,979,456 B1 | 12/2005 | Parikh et al. |
| 6,982,282 B2 | 1/2006 | Lambert et al. |
| 7,030,155 B2 | 4/2006 | Lambert et al. |
| 7,060,285 B2 | 6/2006 | Muller |
| 7,101,568 B2 | 9/2006 | Dang et al. |
| 7,345,093 B2 | 3/2008 | Augustine et al. |
| 7,387,623 B2 | 6/2008 | MacLeod |
| 7,387,791 B2 | 6/2008 | Betageri et al. |
| RE40,493 E | 9/2008 | Straub et al. |
| 2002/0012680 A1 | 1/2002 | Patel et al. |
| 2002/0041896 A1 | 4/2002 | Straub et al. |
| 2003/0099674 A1 | 5/2003 | Chen |
| 2006/0067952 A1 | 3/2006 | Chen |
| 2006/0078618 A1 | 4/2006 | Constantinides et al. |
| 2009/0215882 A1 | 8/2009 | Bouzada et al. |
| 2009/0275526 A1 | 11/2009 | Dash et al. |

FOREIGN PATENT DOCUMENTS

WO    WO9830205    7/1998

OTHER PUBLICATIONS

Taxol Package Insert Document, 2000.*

* cited by examiner

*Primary Examiner* — Sreeni Padmanabhan
*Assistant Examiner* — Uma Ramachandran
(74) *Attorney, Agent, or Firm* — Brian E. Davy; Bret E. Field; Bozicevic, Field & Francis, LLP

(57) ABSTRACT

Taxane pro-emulsion formulations are provided. Pro-emulsion formulations are dried powders that include a taxane, oil, surfactant and sugar alcohol. Also provided are methods of making and using the pro-emulsion formulations, as well as kits that include the pro-emulsion formulations.

17 Claims, No Drawings

TAXANE PRO-EMULSION FORMULATIONS AND METHODS MAKING AND USING THE SAME

CROSS-REFERENCE TO RELATED APPLICATIONS

Pursuant to 35 U.S.C. §119 (e), this application claims priority to the filing dates of: U.S. Provisional Patent Application Ser. No. 61/306,315 filed on Feb. 19, 2010; the disclosure of which application is herein incorporated by reference.

INTRODUCTION

Taxanes constitute a family of naturally occurring diterpene compounds including paclitaxel. Paclitaxel, originally isolated from the bark of the Pacific Yew tree (*Taxus brevifolia*), and its semi-synthetic analogue, docetaxel, are two examples of taxane compounds. Taxanes are active agents that block cell growth by stopping mitosis via microtubule interference.

Taxanes can be used effectively to treat a variety of cancers and have been reported to have therapeutic effects in treating certain inflammatory diseases. Paclitaxel, for example, has been found to have activity against ovarian and breast cancers, as well as against malignant melanoma, colon cancer, leukemias and lung cancer (see, e.g., Borman, Chemical & Engineering News, Sep. 2, 1991, pp. 11-18; The Pharmacological Basis of Therapeutics (Goodman Gilman et al., eds.), Pergamon Press, New York (1990), p. 1239: Suffness, Antitumor Alkaloids, in: "The Alkaloids, Vol. XXV," Academic Press, Inc. (1985), Chapter 1, pp. 6-18: Rizzo et al., J. Pharm. & Biomed. Anal. 8(2):159-164 (1990); and Biotechnology 9:933-938 (October, 1991).

Formulation of taxanes in therapeutically useful carriers, so as to enable the administration of taxanes, is made difficult by the nature of the taxane molecule, which can be poorly soluble in both aqueous and lipid carriers.

SUMMARY

Taxane pro-emulsion formulations are provided. Pro-emulsion formulations are dried powders that include a taxane, an oil, a surfactant and a sugar alcohol. Also provided are methods of making and using the pro-emulsion formulations, as well as kits that include the pro-emulsion formulations.

Accordingly, aspects of the invention include taxane pro-emulsion formulations, where the formulations include a dried powder that includes a taxane; an oil; a surfactant; and a sugar alcohol; where the powder is formulated to produce upon combination with an aqueous medium a clear emulsion having a particle size that is substantially the same as that of the dried powder's precursor emulsion. In some instances, the taxane is described by the formula:

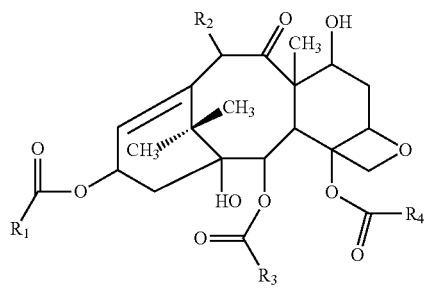

where:

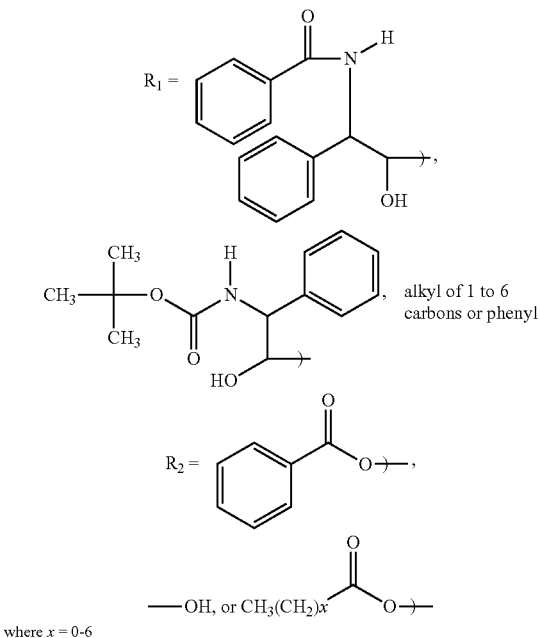

where $x = 0-6$ $R_3$=alkyl of 1 to 6 carbons or phenyl; and $R_4$=alkyl of 1 to 6 carbons or phenyl. In some instances, the taxane is paclitaxel or docetaxel. In some instances, the oil is present in an amount ranging from 0.1 to 10% by weight. In certain embodiments, the oil is selected from the group consisting of soybean oil, a tocopherol and a glycerol ester of a medium chain fatty acid. In some instances, the surfactant is present in an amount ranging from 10 to 70% by weight. Surfactants of interest include non-ionic surfactants, e.g., polysorbate 80. In some instances, the pro-emulsion formulation includes a non-aqueous solvent. When present, the non-aqueous solvent may be present in an amount ranging from 0.1 to 30% by weight. Non-aqueous solvents of interest include proplyene glycol. In some instances, the sugar alcohol is present in an amount ranging from 15 to 80% dry weight. Sugar alcohols of interest include mannitol. In some instances, the pro-emulsion formulation further includes an emulsification enhancer. An emulsification enhancer of interest is oleic acid. In some instances, the particle size is 70 nm or less, including 50 nm or less.

Embodiments of the invention include taxane pro-emulsion formulations that are dried powders which include a taxane (e.g., paclitaxel or docetaxel); soybean oil; polysorbate 80; propylene glycol; and mannitol; wherein the powder is formulated to produce upon combination with an aqueous medium clear emulsion having a particle size that is substantially the same as that of the dried powder's precursor emulsion. In certain instances, the soybean oil is present in an amount ranging from 0.4 to 8% by weight. In certain instances, the polysorbate 80 is present in an amount ranging from 30 to 60% by weight. In certain instances, the propylene glycol is present in an amount ranging from 0.1 to 15% by weight. In certain instances, the mannitol is present in an amount ranging from 25 to 65% dry weight. In certain instances, the pro-emulsion formulation further comprises oleic acid.

Aspects of the invention further include methods of administering a taxane to a subject. The methods include combining a taxane pro-emulsion formulation, e.g., as described above, with an aqueous medium to produce a clear taxane emulsion; and administering the taxane emulsion to the subject. In some instances, the method comprises storing the taxane pro-emulsion formulation for 1 day or longer before contacting the pro-emulsion formulation with the aqueous medium. In some instances, the subject suffers from a cellular proliferative disease.

Aspects of the invention further include clear taxane emulsion compositions. In some instances, the clear taxane emulsion compositions include a taxane; an oil; a surfactant; a sugar alcohol; and water. In some instances, the taxane is described by the formula:

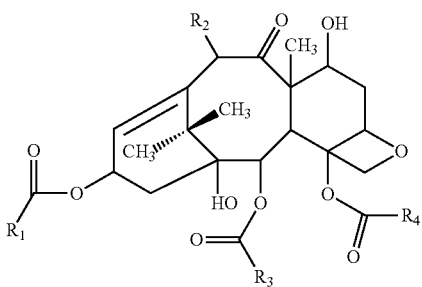

where:

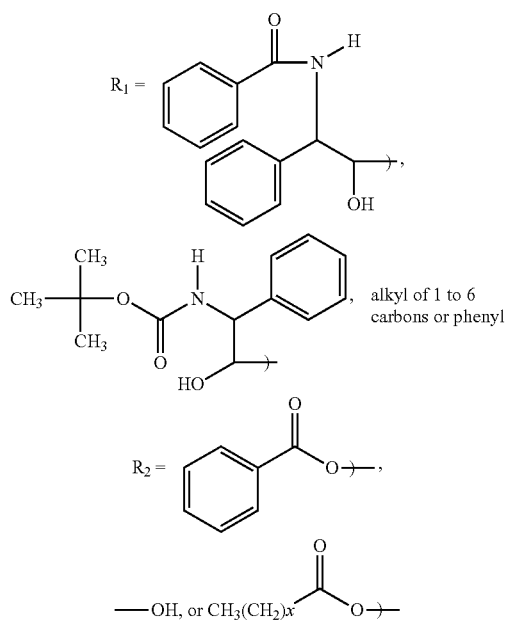

where $x = 0\text{-}6$ $R_3$=alkyl of 1 to 6 carbons or phenyl; and $R_4$=alkyl of 1 to 6 carbons or phenyl. In certain embodiments, the taxane is paclitaxel or docetaxel. In some embodiments, the oil is present in an amount ranging from 0.0007 to 6% by weight. In certain embodiments, the oil is selected from the group consisting of soybean oil, a tocopherol and a glycerol ester of a medium chain fatty acid. In some embodiments, the surfactant is present in an amount ranging from 0.07 to 40% by weight. In some instances, the surfactant is a non-ionic surfactant. In some instances, the non-ionic surfactant is polysorbate 80. In some instances, the emulsion includes a non-aqueous solvent. In some instances, the non-aqueous solvent is present in an amount ranging from 0.1 to 17% by weight. In some instances, the non-aqueous solvent is proplyene glycol. In some instances, the sugar alcohol is present in an amount ranging from 0.1 to 45% dry weight. In some instances, the sugar alcohol is mannitol. In some embodiments, the emulsion formulation further includes an emulsification enhancer, e.g., oleic acid. In some instances, the emulsion has a particle size of 70 nm or less, including 50 nm or less.

Aspects of the invention further include kits that include: (a) a taxane pro-emulsion formulation which is a dried powder comprising: a taxane; an oil; a surfactant; and a sugar alcohol; wherein the powder is formulated to produce upon combination with an aqueous medium a clear emulsion having a particle size that is substantially the same as that of the dried powder's precursor emulsion; and (b) an aqueous medium, e.g., water. In some instances, the taxane is described by the formula:

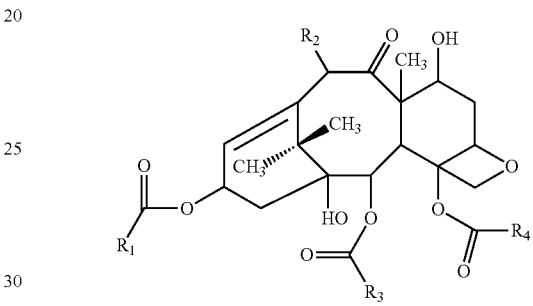

where:

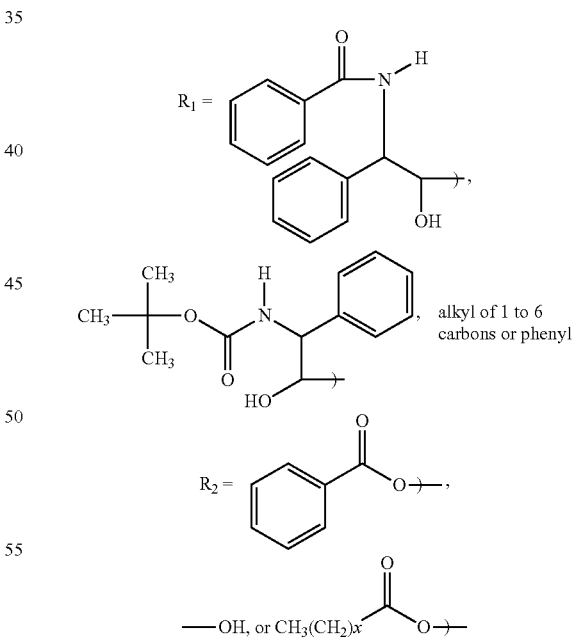

where $x = 0\text{-}6$ $R_3$=alkyl of 1 to 6 carbons or phenyl; and $R_4$=alkyl of 1 to 6 carbons or phenyl. In certain embodiments, the taxane is paclitaxel or docetaxel. In some embodiments, the oil is present in an amount ranging from 0.0007 to 6% by weight. In certain embodiments, the oil is selected from the group consisting of soybean oil, a tocopherol and a glycerol ester of a medium chain fatty acid. In some embodiments, the surfactant is present in an amount ranging from 0.07 to 40% by weight. In some instances, the surfactant is a non-ionic surfactant. In some instances, the non-ionic surfactant is polysorbate 80. In some instances, the emulsion includes a non-aqueous solvent. In some instances, the non-aqueous solvent is present in an amount ranging from 0.1 to 17% by weight. In some instances, the non-aqueous solvent is proplyene glycol. In some instances, the sugar alcohol is present in an amount ranging from 0.1 to 45% dry weight. In some instances, the sugar alcohol is mannitol. In some embodiments, the emulsion formulation further includes an emulsification enhancer, e.g., oleic acid. In some instances, the emulsion has a particle size of 70 nm or less, including 50 nm or less.

DETAILED DESCRIPTION

Taxane pro-emulsion formulations are provided. Pro-emulsion formulations are dried powders that include a taxane, an oil, a surfactant and a sugar alcohol. Also provided are methods of making and using the pro-emulsion formulations, as well as kits that include the pro-emulsion formulations.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following sections, the pro-emulsion formulations and emulsions prepared therefrom, as well as methods using the same, are described first in greater detail, followed by a review of methods for preparing the pro-emulsion formulations and emulsions, as well as kits that may include the formulations.

Taxane Pro-Emulsion Formulations and Emulsions Prepared Therefrom

Aspects of the invention include taxane pro-emulsion formulations. As the formulations are pro-emulsion formulations, they are dried compositions that, upon combination with an aqueous medium, produce a taxane emulsion. The emulsions prepared from the pro-emulsion formulations are liquid preparations that are a suspension of small particles (i.e. globules) of one liquid in a second liquid with which the first liquid will not mix. In certain embodiments, the product emulsions prepared from pro-emulsion formulations of the invention are emulsions of oil and water. As the formulations are emulsions, they are mixtures of two immiscible (e.g. unblendable) fluids, where one fluid (e.g. an oil or water) (the dispersed phase) is dispersed in the other fluid (e.g. the other of the oil or water) (the continuous phase). The water present in the emulsions may be any convenient water, including deinionized water, USP water for injection (WFI), etc.

The product emulsions include a taxane, oil, a surfactant, a non-aqueous solvent, a sugar alcohol and water. In certain embodiments, the product emulsions are clear. By clear is meant that the emulsion is a translucent, if not transparent liquid, i.e., the liquid is pellucid. As such, the emulsion is not cloudy, e.g., as a suspension may appear. Further details regarding the product emulsions that may be prepared from the taxane pro-emulsion precursors are provided below.

As indicated above, the taxane pro-emulsion precursors are dried solid compositions. The dried, solid compositions may take a variety of different formats, such as solid blocks or cakes, or particulate compositions (i.e., powders). For powdered embodiments, the diameter of the particles making up the powder may vary, and in some instances the diameter ranges from 1 μm to 1 cm, such as 1 μm to 5 mm and including 1 μm to 1 mm.

The dried pro-emulsion formulations of embodiments of the invention include at least a taxane, an oil, a surfactant and a sugar alcohol.

Taxanes of interest are diterpene compounds. In some instances, taxanes are compounds described by the formula:

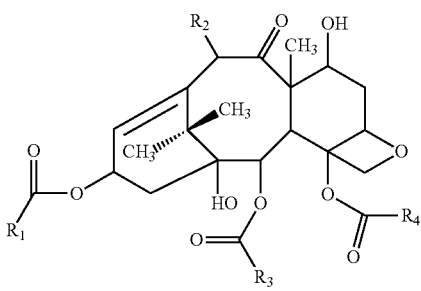

where:

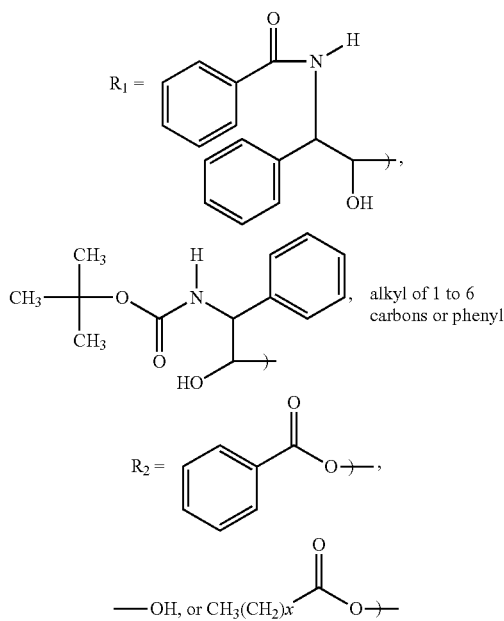

where x = 0-6

$R_3$=alkyl of 1 to 6 carbons or phenyl; and
$R_4$=alkyl of 1 to 6 carbons or phenyl.

In certain embodiments, the taxane is paclitaxel or docetaxel. Taxanes of interest also include, but are not limited to: 7-epitaxol, 7-acetyl taxol, 10-desacetyl-taxol, 10-desacetyl-7-epitaxol, 7-xylosyltaxol, 10-desacetyl-7-glutaryltaxol, 7-N,N-dimethylglycyltaxol, 7-L-alanyltaxol, SB-T-1011, etc. The taxane may be present a free base or salt.

Pro-emulsion formulations include an effective amount of one or more taxanes. By effective amount is meant a dosage sufficient to provide the desired result, e.g., inhibition of cellular proliferation. The effective amount of taxane may vary depending on the particular taxane employed, and in certain embodiments ranges from 0.05 to 5% by weight, such as 0.1 to 3% by weight and including 0.3 to 2% by weight. In certain embodiments, the pro-emulsion formulations include an effective amount of paclitaxel. In certain embodiments, paclitaxel is present in the pro-emulsion formulation in an amount ranging from 0.05 to 5% by weight, such as 0.1 to 2.5% by weight and including 0.3 to 1.0% by weight. In certain embodiments, the pro-emulsion formulations include an effective amount of docetaxel. In certain embodiments, docetaxel is present in the pro-emulsion formulation in an amount ranging from 0.1 to 5% by weight, such as 0.2 to 3% by weight and including 0.5 to 2% by weight.

Also present in the pro-emulsion formulations is an oil component made up of one or more oils. Oils of interest are physiologically acceptable and include, but are not limited to: simple lipids, derived lipids, complex lipids that are derived from natural vegetable oil and fat, animal oil and fat, and mineral oil, or mixtures thereof, where the oils may be naturally occurring or synthetic.

In certain embodiments, the oil includes, but is not limited to soybean oil, olive oil, sesame oil, castor oil, corn oil, peanut oil, safflower oil, grape seed oil, eucalyptus oil, medium-chain fatty acid esters, low-chain fatty acid esters, and the like. Animal oils and fat of interest include, but are not limited to, cod-liver oil, seal oil, sardine oil, docosahexiaenoic acid, and eicosapentaenoic acid. Mineral oils of interest include, but are not limited to, liquid paraffins (e.g. oils derived from n-alkanes), naphthenic oils (e.g. oils based on cycloalkanes), and aromatic oils (e.g. oil based on aromatic hydrocarbons). One or a combination of more than one of these types of oils can be used. For example, some embodiments of the subject emulsion formulations include soybean oil, olive oil, sesame oil, or combinations thereof. Other embodiments include soybean oil, olive oil, or combinations thereof. Highly refined oils and fats are employed in certain embodiments.

Oils of interest also include tocopherols. Tocopherols are a family of natural and synthetic compounds, also known by the generic names tocols or Vitamin E. α-tocopherol is the most abundant and active form of this class of compounds and it has the following chemical structure (Scheme I):

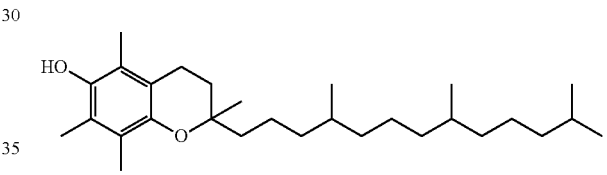

Other members of this class include α-, β-, γ-, and δ-tocotrienols, and α-tocopherol derivatives such as tocopherol acetate, phosphate, succinate, nitotinate and linoleate. Any convenient tocopherol may be present, as desired, including the specific tocopherols listed above.

Oils of interest also include polyol esters of medium chain fatty acids. The term "polyol esters of medium chain fatty acids" is intended to include esters and mixed esters of glycerol, propylene glycol or other open chain polyols such as polyethylene glycol, reacted with medium chain fatty acids, e.g., where the acid has a chain length between 6 and 12 carbon atoms. In some instances, the polyol esters of medium chain fatty acids are triglycerides or diglycerides of the $C_8$-$C_{10}$ fatty acids, e.g., as may be commercially available from the fractionation of coconut oil. Commercially available products of this description are sold under the trade names "Miglyol" and "Captex 300" which are described as having a typical composition of about 68% $C_8$ fatty acid (caprylic) triglyceride and about 28% $C_{10}$ fatty acid (capric) triglyceride with minor levels of $C_6$ and $C_{14}$ fatty acid triglycerides.

In some instances, the amount of oil in the pro-emulsion formulation ranges from 0.05 to 12% by weight, such as 0.1 to 10% by weight and including 0.4 to 8% by weight.

Also present in certain embodiments of the subject pro-emulsion formulations is one or more surfactants. Surfactants of interest include any type of surfactant that can be used for pharmaceutical formulations, including but not limited to, phospholipids, refined phospholipids, nonionic surfactants, or mixtures thereof. Refined phospholipids may include phosphatidylinocytol, phosphatidyl ethanolamine, phosphatidylserine, and sphingomyeline with phosphatidylcholine as a main ingredient. For example, refined phospholipids include egg-yolk lecithin and soybean lecithin. Nonionic surfactants of interest include, but are not limited to, polyethylene glycol, polyoxyalkylene copolymer, and sorbitan fatty acid esters. In some embodiments, the sorbitan fatty acid ester is a polyoxyethylene sorbitan fatty acid ester (e.g., Polyoxyethylene sorbitan tristearate (Tween 65); Polyoxyethylene sorbitan trioleate (Tween 85); Polyethylene glycol 400 monostearate; Polysorbate 60; (Tween 60); Polyoxyethylene monostearate (Myrj 49); Polysorbate 80 (Tween 80); Polysorbate 40 (Tween 40); and Polysorbate 20 (Tween 20)) or sorbitan fatty acid esters (e.g., Sorbitan trioleate (Span 85); Sorbitan tristearate (Span 65); Sorbitan sesquioleate (Arlacel 83); Glyceryl monostearate; Sorbitan monooleate (Span 80); Sorbitan monostearate (Span 60); Sorbitan monopalmitate (Span 40); Sorbitan monolaurate (Span 20)). The amount of surfacant in the pro-emulsion formulation may vary. In some instances, the amount of surfacant in the pro-emulsion formulation ranges from 10 to 70% by weight, such as 20 to 65% by weight and including 30 to 60% by weight. The combination ratio of the oil and the surfactant in the subject pro-emulsion formulations may vary, ranging in some instances from $1/1000$ to $1/2$, such as $1/100$ to $1/5$.

Pro-emulsion formulations of the invention further include one or more sugar alcohols (i.e., polyhydric alcohols). Polyhydric alcohols of interest include, but are not limited to: d-sorbitol, xylitol, ribitol, arabitol, dulcitol, iditol, mannitol, etc. The sugar alcohol may be present in varying amounts, and in some instances ranges from 15 to 80% by weight, such as 25 to 65% by weight.

In some instances, pro-emulsion formulations of the invention further include one or more non-aqueous solvents. Non-aqueous solvents of interest include, but are not limited to: propylene glycol, polypropylene glycol, polyethylene glycol (such as PEG300, 400, 600, etc.), glycerol, ethanol, triacetin, dimethyl isosorbide, glycofurol, propylene carbonate, water, dimethyl acetamide or a mixture thereof. The non-aqueous solvent may be present in varying amounts, and in some instances ranges from 0.1 to 30% by weight, such as 0.1 to 15% by weight.

Certain embodiments of the subject emulsion formulations also include one or more emulsification enhancers. Any type of fatty acid that can be used for pharmaceutical formulations can be used as an emulsification enhancer. Of interest are fatty acids that include from 6 to 22 carbons. Either natural or synthetic, and either saturated fatty acids or unsaturated fatty acids can be used, including but not limited to stearic acid, oleic acid, linoleic acid, palmitic acid, linolenic acid, myristic acid, and the like. In certain embodiments, the emulsion formulation includes a refined fatty acid, e.g., oleic acid. When present, the amount of emulsification enhancer included in the pro-emulsion formulation can vary, and in some instances ranges from 0.1 to 5% by weight, such as 0.1 to 3% by weight.

An aspect of embodiments of the pro-emulsion formulations is that the pro-emulsion formulation is formulated to produce, upon combination with an aqueous medium, an emulsion having a particle size that is substantially the same as that of the dried powder's precursor emulsion. In these instances, the pro-emulsion formulation is prepared from a precursor emulsion, e.g., as described in greater detail below. In this precursor emulsion, the precursor emulsion has a particle size (which refers to the size of the average diameter of the droplets (i.e., globules) of the dispersed phase in the dispersing phase) that may vary, and in certain embodiments ranges from 3 to 100 nm, such as 5 to 70 nm and including 7 to 50 nm. Upon combination of the pro-emulsion with an aqueous medium, e.g., water for injection, saline solution, etc., a final emulsion is prepared in which the particle size is substantially the same as the particle size of the precursor emulsion. As such, the difference of any variation in particle size between the final and precursor emulsions is 50 nm or less, such as 20 nm or less, including 10 nm or less, e.g., 5 nm or even 3 nm or less. In some instances, the particle size of the final emulsion ranges from 3 to 70 nm, such as 5 to 50 nm and including 7 to 30 nm. Of interest in certain embodiments are product emulsions that are clear (e.g., as described above) and have a particle size of 70 nm or less, such as 50 nm or less, including 30 nm or less.

Methods of Preparing Taxane Pro-Emulsion Formulations

Pro-emulsion formulations may be prepared from precursor emulsions. Precursor emulsions may be prepared by combining the components of the pro-emulsion formulation (e.g., as described above) with an amount of an aqueous medium, e.g., water, under conditions sufficient to produce a precursor emulsion and then separating water from the precursor emulsion to produce the desired pro-emulsion, e.g., as described above.

The precursor emulsion formulation may be prepared according to any convenient protocol. As such, the components of the desired pro-emulsion formulation may be combined with an aqueous medium, e.g., water, under conditions sufficient to produce the desired precursor emulsion. Accordingly, an amount of a taxane component, an oil component, a surfactant component, a non-aqueous solvent component and a sugar alcohol component may be combined with water under conditions sufficient to produce a precursor emulsion. In the precursor emulsion, the amount of taxane (e.g., as described above) may vary, ranging in some instances from 0.1 to 5, such as 0.5 to 2 mg/ml. The amount of oil (e.g., as described above) may vary, ranging in some instances from 0.1 to 100, such as 1 to 10 mg/ml. The amount of surfactant (e.g., as described above) may vary, ranging in some instances from 25 to 400, such as 50 to 200 mg/ml. The amount of non-aqueous solvent (e.g., as described above) may vary, ranging in some instances (when present) from 0.1 to 50, such as 0.1 to 25 mg/ml. The amount of sugar alcohol (e.g., as described above) may vary, ranging in some instances (when present) from 25 to 300, such as 50 to 150 mg/ml.

The precursor emulsion may be prepared using any convenient protocol. The components may be combined in any convenient order with the aqueous medium. Aqueous media of interest include, but are not limited to: deionized water, USP water for injection (WFI), etc. Certain of the components may be combined with each other, and then combined with the aqueous medium, or all of the components may be combined at substantially the same time. Combination may include various manners of agitation, e.g., stirring, etc., in order to produce the desired precursor emulsion. In certain embodiments, the preparation methods include mixing an active agent, water and oil, and emulsifying the mixture. For example, an injection solvent, e.g., WFI, can be added to a smooth mixture of a suitable oil. Initially, the mixture can be roughly emulsified. For example, for rough emulsification, Homomixer (Mizuho Industrial Co., Ltd.) or High Flex Disperser (SMT) can be used. After the mixture is roughly emulsified, the mixture can be finely emulsified, e.g., by using a high pressure emulsification machine. For fine emulsification, a high pressure homogenizer such as Gaulin Homogenizer (APV-SMT) and Microfluidizer (Microfluidics, Newton, Mass.) can be used. In addition, for fine emulsification, the emulsion formulation may be treated by the emulsification machine more than once, such as 2 to 50 times, for example 5 to 20 times, at a pressure ranging from 500 to 850 kg/cm². The preparation methods can be carried out at room temperature or at a temperature lower than room temperature. In certain embodiments, the preparation methods include flushing the emulsification machine with nitrogen gas. Specific examples of protocols for preparing precursor emulsions are provided in the Experimental section, below.

Following preparation of the precursor emulsion, water may be separated from the precursor emulsion to produce the desired pro-emulsion. As such, the precursor emulsion may be dried to produce the desired pro-emulsion formulation. The precursor emulsion may be dried using any convenient protocol, including but not limited to: evaporation, lyophilization, etc. Where evaporation is employed, the precursor formulation may be maintained for a sufficient period of time at a suitable temperature to produce the desired pro-emulsion formulation. In some instances, the precursor formulation is maintained at a temperature ranging from 20 to 80° C., such as 40 to 60° C., for a time ranging from 10 to 120 min, such as 20 to 60 min, to produce the desired pro-emulsion.

In some instances, the precursor emulsion is dried to produce a bulk amount of pro-emulsion formulation. Following production of the bulk amount of pro-emulsion formulation, a dosage of the bulk amount may be obtained and combined with an aqueous medium to produce a dosage of injectable final emulsion. Where desired, the bulk amount of pro-emulsion formulation may be stored for a period of time prior to apportionment into a single dosage and use, where this storage time may vary, and in certain embodiments ranges from 5 min to 24 hr, such as from 5 min to 12 hr and including from 5 min to 6 hr.

Where desired, an amount of the precursor emulsion may be loaded into an individual dosage container, e.g., vial, which holds the pro-emulsion and keeps it sterile during shipping, storage, and handling. Before or during the loading stage, the emulsion can be passed through a sub-micron sterilizing filter which has a sufficiently small pore size to remove any bacteria or viruses. As used herein, the term "vial" refers to any stiff-walled container that is used to hold the pro-emulsion formulation. In some instances the vials are made of clear glass, which allows several advantages, including visual inspection of the enclosed drug (to ensure that it is still in a clean, non-caramelized, non-collapsed form, when it is ready for use) and of the container itself (to ensure that it does not have a hairline crack in one of the walls, which could jeopardize or destroy sterility of the enclosed drug). Various types of pharmaceutical vials are known. Single-chamber vials can be sealed with rubber or plastic plugs that will allow a hypodermic needle to be pushed through the rubber seal. Alternately, a single-chamber vial can be made of a brittle and easily breakable material, inside a sealed bag that can contain an aqueous solution (such as physiological saline or a dextrose solution, in an intravenous infusion bag); if this type of vial is broken, it will release its contents into the still-sealed bag, for mixing. In yet other embodiments, two-chamber vials or analogous structures, e.g., as described in Published United States Application Publication No. 20030099674 and U.S. Pat. No. 4,781,354 may be employed. Following loading of the precursor emulsion into the container, the precursor emulsion may be dried in the container to product a pro-emulsion formulation present in the container, e.g., vial. Where desired, the pro-emulsion formulation dosages may be stored for an extended period of time prior to reconstitution and use, where this storage time may vary, and in certain embodiments is 1 week or longer, such as 1 month or longer, including 3 months or longer, e.g., 6 months or longer, including 1 year or longer. When stored, any suitable storage conditions may be employed.

Taxane Product Emulsion Formulations and Methods of Use

Following preparation of the pro-emulsion formulation, e.g., as described above, at the time of desired administration to a subject, a dosage amount of the pro-emulsion may be combined with an aqueous medium to prepare a product emulsion formulation that is suitable for use. The dosage amount of the pro-emulsion formulation may be combined with any suitable aqueous medium, where aqueous mediums of interest include, but are not limited to: deinionized water, USP water for injection (WFI), salines, etc. The liquids to solids ratio employed during preparation of the product emulsion may vary, and in certain embodiments ranges from 0.5 to 300, such as 1 to 200 and including 2 to 150. In some instances, the dosage amount of pro-emulsion formulation that is combined with the aqueous medium ranges from 100 to 1200 g, such as 300 to 600 g and the amount of aqueous medium that is combined with the dosage amount ranges from 100 to 1200 ml, such as 250 to 600 ml.

Where desired, the pro-emulsion formulation may be stored for a period of time prior to combination with the aqueous medium. This storage time may vary, ranging in some instances from 5 min. to 24 hr, such as 5 min. to 12 hr and including 5 min to 6 hr. While the storage conditions may vary, in certain instances the storage conditions are characterized by a temperature ranging from 5 to 60° C., such as 8 to 40° C. The activity of the taxane active agent is preserved during the storage period, such that the pro-emulsion formulations are storage stable. As such, the activity of the taxane active agent in the reconstituted product emulsion following storage is substantially the same as that in the precursor emulsion prior to drier, where the magnitude of any difference in activity may be 15% or less, such as 10% or less, including 5% or less, e.g., as measured according to HPLC performed as summarized in the following table.

| | |
|---|---|
| Measurement Wavelength | UV = 230 nm |
| Column | MERCK Lichrospher RP-18 5µ 4.0 × 125 (ODS type) |
| Column temperature | 40° C. |
| Mobile phase | Methanol/Water 65/35 vol. % |
| Sample volume | 20 µl |
| Measurement time | PAC 13 min. DOC 20 min. |
| Internal reference | PAC butyl benzoate 0.1 mg/ml DOC isopentyl benzoate 0.1 mg/ml |

The combination protocol may vary, where agitation may be employed, e.g., by stirring, by kneading a bag that includes both the emulsion and the aqueous medium, etc.

The product taxane emulsion formulations that are produced upon reconstitution of the pro-emulsion formulation with the aqueous medium can have a physiologically acceptable pH. In certain embodiments, the pH of the emulsion formulations ranges from 2.5 to 8, such as from 3 to 7, including from 3.5 to 6. The product taxane emulsion formulations are clear formulations. The concentration of the taxane in the product emulsion may vary, ranging in some embodiments from 0.05 to 10 mg/ml, such as 0.2 to 3 mg/ml.

Methods of using the product taxane emulsion formulations include administering an effective amount of the taxane emulsion formulation to a subject in order to treat the subject for a target condition of interest. By "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom, associated with the condition being treated, such as pain. As such, treatment also includes situations where the condition is completely inhibited, e.g., prevented from happening, or stopped, e.g., terminated, such that the subject no longer experiences the condition. As such, treatment includes both preventing and managing a condition.

In practicing the methods, the emulsion formulations disclosed herein can be parenterally administered to a subject. By "parenteral administration" is meant administration by a protocol that delivers a quantity of the emulsion formulation to the subject, e.g., a patient suffering from post-surgical pain, by a route other than the digestive tract. Examples of parenteral administration include, but are not limited to, intramuscular injection, intravenous injection, transdermal absorption, inhalation, and the like. In certain embodiments, parenteral administration is by injection using an injection delivery device. The amount of emulsion formulation that is administered to the subject may vary depending on a number of factors, such as patient specifics, nature of condition, nature of taxane active agent, etc. In certain embodiments, the volume of emulsion that is administered to a subject may range from 100 to 1000 ml, such as 200 to 600 ml. The time period over which this volume is administered may vary, ranging from 0.5 to 6 hr, such as from 1 to 3 hr. Dosages administered to a subject during a given procedure may also vary, ranging in some instances from 20 to 500 mg/m$^2$, such as from 50 to 300 mg/m$^2$.

In some instances, individuals to which the compositions of the invention are administered are individuals that have been diagnosed as being in need of the subject methods. In certain embodiments, the subject methods include a diagnostic step. Individuals may be diagnosed as being in need of the subject methods using any convenient protocol. In addition, individuals may be known to be in need of the subject methods, e.g., they are suffering from a target disease condition (e.g., cellular proliferative disease, prior to practicing the subject methods. Diagnosis or assessment of target condition can be performed using any convenient diagnostic protocol.

Methods of the invention may further include assessing the efficacy of the treatment protocol that includes administration of the taxane emulsion formulation. Assessing the efficacy of treatment may be performed using any convenient protocol.

Taxane emulsion formulations of the invention may be administered to a variety of different types of subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

Utility

The subject emulsion formulations and methods find use in a variety of applications, including the treatment of subjects suffering from cellular proliferative disease conditions. Cellular proliferative diseases that may be treated with compositions of the invention include, but are not limited to: carcinomas, myelomas, neuroblastomas, or sarcomas, of the brain, breast, lung, colon, prostate or ovaries, as well as leukemias or lymphomas. Specific disease conditions of interest include, but are not limited to, human ovarian cancer, breast cancer, malignant lymphoma, lung cancer, melanoma, and Kaposi's sarcoma.

Kits

Also provided are kits that find use in practicing the subject methods, as described above. For example, kits for practicing the subject methods may include a quantity of the pro-emulsion formulation, present in unit dosages, e.g., vials, or a multi-dosage format. As such, in certain embodiments, the kits may include one or more unit dosages (e.g., vials) of the pro-emulsion formulation. The term "unit dosage", as used herein, refers to physically discrete units suitable as unitary dosages for human and animal subjects, each unit containing a predetermined quantity of the subject pro-emulsion formulation calculated in an amount sufficient to produce the desired effect. The amount of the unit dosage of the subject emulsion formulation depends on various factors, such as the particular active agent employed, the effect to be achieved, and the pharmacodynamics associated with the active agent in the subject. In yet other embodiments, the kits may include a single multi-dosage amount of the emulsion formulation.

In certain embodiments, the kits may further include an amount of an aqueous medium suitable for use in reconstitution of the taxane emulsion. The aqueous medium may be any convenient aqueous medium, such as described above, present in any suitable container, e.g., an IV bag.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., one or more pieces of paper on which the information is printed, in the packaging of the kit, in a package insert, etc. The instructions may be present on a computer readable medium, e.g., diskette, CD, DVD, etc., on which the information has been recorded. The instructions may be present on a website, which may be used via the internet to access the information at a removed site. Other convenient means are possible and may be included in the kits.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Experimental

A. Paclitaxel Formulation

| Component | Amount |
| --- | --- |
| paclitaxel | 100 mg |
| polysorbate 80 (Tween 80) | 10,000 mg |
| propylene glycol | 2,000 mg |
| soybean oil | 100 mg |
| Mannitol | 10,000 mg |
| Diameter of precursor emulsion | 11.7 nm |
| Diameter of the final emulsion | 17.0 nm |

In preparing the dried emulsion precursor formulation, 100 mg paclitaxel is combined with 2000 mg propylene glycol, and heated to 50° C. with ultrasound. The resultant mixture is combined with 10,000 mg polysorbate 80 and 100 mg soybean oil, and stirred while applying heat. The resultant mixture is then stirred with a high speed stirrer (12000 rpm×15 min) while the temperature of the mixture is maintained at 60° C. and hot water (temperature 60° C.) is added to bring the volume to 100 ml. 10,000 g mannitol are then added and the mixture is stirred until the mannitol is dissolved. 50 ml of the resultant solution is placed into a vial and sealed with a cap. The vial is sterilized at a temperature of 120° C. for 12 minutes and then allowed to cool to room temperature. After sterilized, liquid in vial is removed with an evaporator to obtain a powder (50° C.×1 hr). The resultant powder is the dried paclitaxel emulsion precursor formulation.

At time of use, the resultant powder is combined with water to obtain a clear emulsion solution suitable for injection.

The following additional formulations were also prepared using the protocol described above.

| Component | Amount | Amount | Amount |
| --- | --- | --- | --- |
| paclitaxel | 100 mg | 100 mg | 100 mg |
| polysorbate 80 (Tween 80) | 8,000 mg | 8,000 mg | 10,000 mg |
| propylene glycol | 0 mg | Glycerine 2,210 mg | 2,000 mg |
| soybean oil | 100 mg | 100 mg | 100 mg |
| Mannitol | 10,000 mg | 10,000 mg | 5,000 mg |
| Diameter of precursor emulsion | 11.0 nm | 11.9 nm | 18.8 nm |
| Diameter of the final emulsion | 15.6 nm | 14.0 nm | 19.6 nm |

B. Docetaxel Formulation

| Component | Amount |
| --- | --- |
| docetaxel | 50 mg |
| polysorbate 80 (Tween 80) | 5000 mg |
| propylene glycol | 500 mg |
| oil | soybean oil 50 mg |
| oleic acid | 120 mg |
| mannitol | 5,000 mg |
| Diameter of precursor emulsion | 13.7 nm |
| Diameter of the final emulsion | 17.1 nm |

In preparing the dried emulsion precursor formulation, 50 mg docetaxel is combined with 120 mg oleic acid, 500 mg propylene glycol and 5,000 mg polysorbate 80, and heated to 50° C. with ultrasound. The resultant mixture is combined with 50 mg soybean oil, and stirred while applying heat. The resultant mixture is then stirred with a high speed stirrer (11,000 rpm×7 min) while the temperature of the mixture is maintained at 60° C. and hot water (temperature 60° C.) is added to bring the volume to 50 ml. 5,000 mg mannitol are then added and the mixture is stirred until the mannitol is dissolved. 10 ml of the resultant solution is placed into a vial and sealed with a cap. The vial is sterilized at a temperature of 120° C. for 12 minutes and then allowed to cool to room temperature. After sterilized, liquid in vial is then removed with an evaporator to obtain a powder (50° C.×1 hr). The resultant powder is the dried docetaxel emulsion precursor formulation.

At time of use, the resultant powder is combined with water to obtain a clear emulsion solution suitable for injection.

The following additional formulations were also prepared using the protocol described above.

| Component | Amount | Amount |
| --- | --- | --- |
| docetaxel | 50 mg | 50 mg |
| polysorbate 80 (Tween 80) | 2500 mg | 5000 mg |
| propylene glycol | 500 mg | 1,100 mg |
| oil | soybean oil 50 mg | glycerol ester of a medium chain fatty acid 100 mg |
| oleic acid | 0 mg | 120 mg |
| mannitol | 5,000 mg | 5,000 mg |
| Diameter of precursor emulsion | 12.9 nm | 11.1 nm |
| Diameter of the final emulsion | 12.1 nm | 17.1 nm |

| Component | Amount | Amount | Amount | Amount |
| --- | --- | --- | --- | --- |
| paclitaxel | 100 mg | 100 mg | 100 mg | 200 mg |
| polysorbate 80 (Tween 80) | 10,000 mg | 8,000 mg | 10,000 mg | 10,000 mg |
| propylene glycol | Phosphate buffer (pH 6.2) | 0 mg | 0 mg | 0 mg |
| soybean oil | 100 mg | 1,000 mg | Tocopherol 100 mg | glycerol ester of a medium chain fatty acid 100 mg |
| Mannitol | 10,000 mg | 10,000 mg | 10,000 mg | 10,000 mg |
| Diameter of precursor emulsion | 12.2 nm | 15.0 nm | 13.1 nm | 8.9 nm |
| Diameter of the final emulsion | 15.8 nm | 15.7 nm | 14.5 nm | 13.0 nm |

C. Administration

The following criteria is used to measure the response of patients having breast cancer to treatment using an embodiment of the present invention:

Partial Remission (PR): Greater than 50% decrease in the sum of the products of the diameters of all measurable lesions for at least one month.

Minor Remission (MR): 25 to 50% decrease in the sum of the products of the diameters of all measurable lesions for at least one month.

Progressive Disease (PD): 25% or greater progression in the sum of the products of the diameter of any measurable lesion over one cycle of chemotherapy or the appearance or any, new lesion consistent with metastatic disease.

In using the above described emulsion precursors, the dried emulsion precursor formulation is reconstituted in an appropriate aqueous medium to provide a clear emulsion suitable for injection. The clear emulsion provides a concentration sufficient to supply between 17.5 and 35 mg of taxane per square meter (based on the body surface area of the patient) over a 6 hour period. The clear emulsion is prepared between 30 and 60 minutes prior to beginning each infusion. The clear emulsion is prepared in a polypropylene lined semi-rigid container, in a volume of 500 ml.

The container with the clear emulsion is connected to an IV pump via a polyethylene tube. An IVEX-HP In Line Filter Set-SL, 15", Abbott model #4525 with a pore size of 0.22 microns is then attached to the IV pump via a polyethylene line-tubing. The in-line filter is then connected to the subject's central access device.

The clear emulsion is infused over a 6 hour period, controlled by the IV pump. The procedure is repeated three more times, for a total 18 hour infusion. The final dose that is achieved is between 70 and 140 mg/m$^2$/18 hours. This infusion procedure is repeated every 21 days, while patients are monitored for a response after every two cycles. If a patient exhibits a toxic or allergic reaction to a dose of paclitaxel, the dosage is lowered until tolerated. The cycles are continued until a patient exhibits disease progression or is stable for 4-6 cycles. After treatment of the patients with the above-described clear emulsion at a rate of between 70 and 140 mg/m$^2$/18 hrs, every 21 days, patients are observed for response after every two cycles.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A taxane proemulsion formulation comprising a dried powder comprising a taxane wherein the taxane is described by the formula,

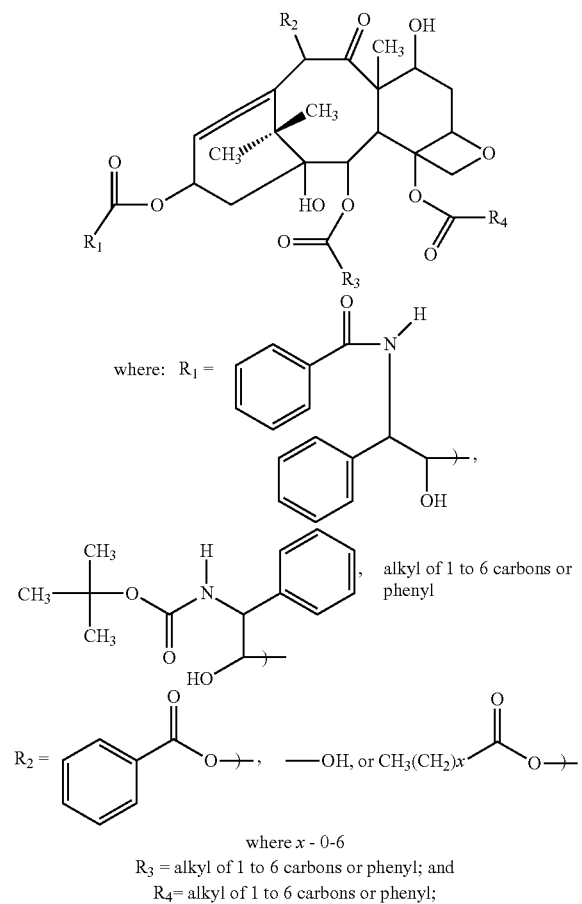

where x - 0-6
$R_3$ = alkyl of 1 to 6 carbons or phenyl; and
$R_4$ = alkyl of 1 to 6 carbons or phenyl;

an oil present in an amount ranging from 0.1-10% by weight;
a surfactant present in an amount ranging from 10-70% by weight; and
a sugar alcohol;
wherein the powder is formulated to produce upon combination with an aqueous medium a clear emulsion having a particle size 70 nm or less, that is substantially the same as that of the dried powder's precursor emulsion.

2. The pro-emulsion formulation according to claim 1, wherein the taxane is paclitaxel.

3. The pro-emulsion formulation according to claim 1, wherein the taxane is docetaxel.

4. The pro-emulsion formulation according to claim 1, wherein the oil is selected from the group consisting of soybean oil, a tocopherol and a glycerol ester of a medium chain fatty acid.

5. The pro-emulsion formulation according to claim 1, wherein the surfactant is a non-ionic surfactant.

6. The pro-emulsion formulation according to claim 5, wherein the non-ionic surfactant is polysorbate 80.

7. The pro-emulsion formulation according to claim 1, wherein the pro-emulsion formulation includes a non-aqueous solvent.

8. The pro-emulsion formulation according to claim 7, wherein the non-aqueous solvent is present in an amount ranging from 0.1 to 30% by weight.

9. The pro-emulsion formulation according to claim 7, wherein the non-aqueous solvent is proplyene glycol.

10. The pro-emulsion formulation according to claim 1, wherein the sugar alcohol is present in an amount ranging from 15 to 80% dry weight.

11. The pro-emulsion formulation according to claim 9, wherein the sugar alcohol is mannitol.

12. The pro-emulsion formulation according to claim 1, wherein the pro-emulsion formulation further comprises an emulsification enhancer.

13. The pro-emulsion formulation according to claim 12, wherein the emulsification enhancer is oleic acid.

14. A taxane proemulsion formulation comprising a dried powder comprising a taxane wherein the taxane is described by the formula,

[chemical structure of taxane with substituents $R_1$, $R_2$, $R_3$, $R_4$]

where: $R_1$ = [structure], alkyl of 1 to 6 carbons or phenyl $R_2$ = [structures], —OH, or $CH_3(CH_2)_x$ [structure]

where $x$ = 0-6
$R_3$ = alkyl of 1 to 6 carbons or phenyl; and
$R_4$ = alkyl of 1 to 6 carbons or phenyl;

soybean oil present in an amount ranging from 0.1-10% by weight;

polysorbate 80 present in an amount ranging from 10-70% by weight;

propylene glycol and mannitol;

wherein the powder is formulated to produce upon combination with an aqueous medium a clear emulsion having a particle size 70 nm or less, that is substantially the same as that of the dried powder's precursor emulsion.

15. A method of administering a taxane to a subject, the method comprising:

(a) combining a taxane pro-emulsion formulation according to claim 1 with an aqueous medium to produce a clear taxane emulsion; and (b) administering the taxane emulsion to the subject.

16. A kit comprising: (a) a taxane pro-emulsion formulation as in claim 1; and (b) an aqueous medium.

17. The pro-emulsion formulation according to claim 1, wherein an emulsion produced upon combination of the powder with an aqueous medium comprises lipid particles consisting of liquid globules.

* * * * *

UNITED STATES PATENT AND TRADEMARK OFFICE
CERTIFICATE OF CORRECTION

PATENT NO.       : 8,569,357 B2  Page 1 of 1
APPLICATION NO. : 13/030495
DATED            : October 29, 2013
INVENTOR(S)      : Nabeta Kiichiro It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 243 days.

Signed and Sealed this
Twenty-third Day of May, 2017

Michelle K. Lee
*Director of the United States Patent and Trademark Office*